(12) United States Patent
Sembo et al.

(10) Patent No.: US 6,541,512 B2
(45) Date of Patent: Apr. 1, 2003

(54) PREVENTION OF PEST FEED HARM ON A FIBROUS PRODUCT

(75) Inventors: Satoshi Sembo, Takarazuka (JP); Masayo Sugano, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/848,217

(22) Filed: May 4, 2001

(65) Prior Publication Data

US 2001/0049390 A1 Dec. 6, 2001

(30) Foreign Application Priority Data

May 8, 2000 (JP) .......................... 2000-134490

(51) Int. Cl.[7] .................... A01N 43/08; A61K 31/34
(52) U.S. Cl. ...................... 514/471; 514/472
(58) Field of Search .................. 514/471, 472

(56) References Cited

U.S. PATENT DOCUMENTS 5,434,181 A  7/1995  Kodaka et al. ............. 544/212
5,532,365 A  7/1996  Kodaka et al. ............. 544/212

FOREIGN PATENT DOCUMENTS

| CA | 2273545 | * 12/1999 |
| EP | 0 210 416 A1 | 2/1987 |
| EP | 0 387 663 A1 | 9/1990 |
| EP | 0 860 841 A2 | 8/1998 |
| JP | 08 217609 A | 8/1996 |
| JP | 08 217610 A | 8/1996 |
| JP | 10-139604 | 5/1998 |
| JP | 11-322511 | 11/1999 |

* cited by examiner

*Primary Examiner*—Alton Pryor
(74) *Attorney, Agent, or Firm*—Birch, Stewart, Kolasch & Birch, LLP.

(57) ABSTRACT

The present invention provides a method of preventing pest feed harm on a fibrous product, a composition preventing pest feed harm on a fibrous product and uses of 1-methyl-2-nitro-3-[(3-tetrahydrofuryl)methyl]guanidine for preventing pest feed harm on a fibrous product. The method comprises applying to a fibrous product, an effective amount of 1-methyl-2-nitro-3-[(3-tetrahydrofuryl)methyl] guanidine. The composition comprises a carrier and as an active ingredient 1-methyl-2-nitro-3-[(3-tetrahydrofuryl) methyl]guanidine.

4 Claims, No Drawings

PREVENTION OF PEST FEED HARM ON A FIBROUS PRODUCT

TECHNICAL FIELD OF THE INVENTION

The present invention relates to methods of preventing pest feed harm on a fibrous product and compositions preventing pest feed harm on a fibrous product.

BACKGROUND OF THE INVENTION

It is known that certain pests, such as the larvae of pests, feed on fibrous products, leaving pest feed harm on the fibrous product. In enclosed storage spaces of dress cabinets, empenthrin has been heretofore well utilized to maintain for an extended amount of time a pesticidal and pest repellent effect. To provide the pesticidal and pest repellent effect, empenthrin is usually set at the targeted area and allowed to continuously vaporize. Such a pest repellency effect typically allows empenthrin to be utilized to prevent pest feed harm on fibrous materials kept in small and enclosed storage spaces. It has been conventional rule of thumb that a compound necessitates a pest repellency effect to sufficiently prevent the pest feed harm on fibrous materials.

In utilizing empenthrin in a larger storage space, empenthrin has been inefficient in that a large amount of empenthrin is needed to sufficiently prevent pest feed harm on the fibrous products. A compound that efficiently prevents the pest feed harm in such larger storage spaces would be useful. This is particularly so, since it is becoming more popular to store fibrous products in larger storing places such as in walk-in closets or in a somewhat wide-open space such as in directly hanging clothes in a room.

Such inefficiencies also generally disqualify empenthrin as an effective compound preventing the pest feed harm on fibrous products, when the fibrous products include furnishings such as carpet, floor rugs and the like. The furnishings are generally placed in wide-open spaces in which a large amount of empenthrin is needed to prevent the pest feed harm thereon. It would be useful to provide an efficient compound that can prevent the pest feed harm in such wide-open spaces.

U.S. Pat. No. 5,532,365 describes the compound 1-methyl-2-nitro-3-[(3-tetrahydrofuryl)methyl]guanidine as having a pesticidal controlling effect directed to various pests. JP-10-139604A describes that because 1-methyl-2-nitro-3-[(3-tetrahydrofuryl)methyl]guanidine has no pest repellency effect, 1-methyl-2-nitro-3-[(3-tetrahydrofuryl)methyl]guanidine can completely exterminate insanitary pests such as mosquitoes, house flies, cockroaches and the like.

SUMMARY OF THE INVENTION

The present invention provides methods of preventing pest feed harm on a fibrous product and compositions preventing pest feed harm on a fibrous product. The methods comprise applying to a fibrous product, an effective amount of 1-methyl-2-nitro-3-[(3-tetrahydrofuryl)methyl] guanidine. The compositions comprise a carrier and as an active ingredient 1-methyl-2-nitro-3-[(3-tetrahydrofuryl) methyl]guanidine. The present invention also provides uses of 1-methyl-2-nitro-3-[(3-tetrahydrofuryl)methyl]guanidine for preventing pest feed harm on a fibrous product.

DETAILED DESCRIPTION OF THE INVENTION

The methods and compositions of the present invention can efficiently prevent pest feed harm on a fibrous product, when the fibrous product is in an enclosed storage space, in a large storage space or in a wide-open space. In efficiently preventing pest feed harm on the fibrous product, the methods and compositions of the present invention typically achieve a prevention of the pest feed harm continuously over an extended period. Further, the methods and compositions of the present invention avoid causing discomfort to humans or animal, when the human or the animal is extensively in contact with the treated fibrous product. When applied to the fibrous material, 1-methyl-2-nitro-3-[(3-tetrahydrofuryl) methyl]guanidine can also be innocuously supported on the fibrous material.

In the present method, 1-methyl-2-nitro-3-[(3-tetrahydrofuryl)methyl]guanidine can be applied to the fibrous product as is, but can also be formulated into a composition and then applied to then fibrous product. When formulated into a composition, 1-methyl-2-nitro-3-[(3-tetrahydrofuryl)methyl]guanidine is typically formulated with an a solid carrier, a liquid carrier, adjuvant or the like. Such compositions may contain 1-methyl-2-nitro-3-[(3-tetrahydrofuryl)methyl]guanidine at an amount of about 0.005 to 50% by weight, but is not limited thereto since the effective amount of 1-methyl-2-nitro-3-[(3-tetrahydrofuryl) methyl]guanidine therein may vary with the specific composition form thereof or the specific method employed to prevent pest feed harm.

As such compositions, for example, there can be mentioned liquid compositions such as emulsifiable concentrates, oily compositions and suspensions; wettable powders, microencapsulated compositions, foamy compositions, aerosols and the like.

Such formulations can be formulated with conventional techniques, for example, by mixing 1-methyl-2-nitro-3-[(3-tetrahydrofuryl)methyl]guanidine with the solid carrier or liquid carrier. If needed, there may be mixed therewith an adjuvant such as an emulsifier, sticking agent and the like.

As examples of the carrier, the following are mentioned. As the solid carrier, for example, there is mentioned naturally-occurring or synthetic minerals, such as clays, kaolin, talc, bentonite, sericite, quartz, sulfur, active carbon, calcium carbonate, diatomaceous earth, pumice, calcite, meerschaum, dolomite, silica, alumina, vermiculite and pearlite; fine granules such as sawdust, corncob, coconut shell and tobacco foliage; gelatin; vaseline; methylcellulose; lanolin; lard; cyclodextrin and the like. As liquid carriers, for example, there is mentioned aromatic or aliphatic hydrocarbons such as xylene, toluene, alkylnaphthalene, phenylxylylethane, kerosene, gas oils, hexane and cyclohexane; halogenated hydrocarbons such as chlorobenzene, dichloromethane, dichloroethane and trichloroethane; alcohols such as methanol, ethanol, isopropyl alcohol, butanol, hexanol, benzyl alcohol and ethylene glycol; ethers such as diethyl ether, ethyleneglycol dimethyl ether, diethyleneglycol monomethyl ether, diethyleneglycol monoethyl ether, propyleneglycol monomethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrile and isobutylonitrile; acid amides such as dimethylsulfoxide, N,N-dimethylformamide and N,N-dimethylacetamide; botanical oils such as soy bean oil and cotton seed oil; essential oils such as orange oil, hyssop oil and lemon oil; water and the like.

Further, it is worth noting that the compositions may also utilized therein a propellant. Exemplarily of the compositions that may utilize the propellant therein include the foamy compositions, aerosols and the like. As the propellant in such foamy compositions or in such aerosols, for example, there is mentioned propane gas, butane gas, chlorofluorohydrocarbons, liquefied petroleum gases, dimethyl ether and the like.

As the adjuvants, for example, there is mentioned nonionic emulsifiers such as polyoxyethylene fatty acid esters and polyoxyethylene fatty acid alcohol ethers; ionic emulsifiers such as alkylsulfonate salts, alkylsulfate salts and arylsulfonate salts; dispersing agents such as ligninsulfonate salts and methylcellulose; sticking agents such as carboxymethylcellulose, gum arabic, polyvinyl alcohol and polyvinylacetate; coloring agents such as iron oxide, titanium oxide, Persian blue, alizarine dye, azo dye and phthalocyanine dye; buffers such as acetate salts and sodium citrate; pH controlling agents such as citric acid, adipic acid, fumaric acid, malic acid, gluconic acid, and acetic acid; anti-corrosive agents; preservatives; antioxidants such as butylhydroxyanisol (BHA), dibutylhydroxytoluene (BHT), tocopherol and γ-oryzanol; deodorants and the like.

In the present invention, as fibrous products subject to prevention of pest feed harm, for example, there is mentioned clothings, textiles, floor rugs, carpets, floor mats, sofas, beds, cushions, chairs comprising fibers and the like. Such fibrous products typically utilize therein in fibers that pests feed on. Examples of such fibers include wools such as kashmir, wool muslin and sheep wool, cotton, furs, hemp, silk and the like.

In applying, 1-methyl-2-nitro-3-[(3-tetrahydrofuryl)methyl]guanidine may be applied to the fibrous product such that 1-methyl-2-nitro-3-[(3-tetrahydrofuryl)methyl] guanidine is supported in the fibrous product. In such cases, 1-methyl-2-nitro-3-[(3-tetrahydrofuryl)methyl]guanidine may be applied to the whole fibrous product. When applying, 1-methyl-2-nitro-3-[(3-tetrahydrofuryl)methyl] guanidine or the composition thereof may be diluted with an appropriate amount of water and then applied to the fibrous product.

Typically, the application to the fibrous product has an effective amount of 1-methyl-2-nitro-3-[(3-tetrahydrofuryl) methyl]guanidine applied thereto, such as from 1 to 5000 mg of 1-methyl-2-nitro-3-[(3-tetrahydrofuryl)methyl]guanidine or from 5 to 1000 mg of 1-methyl-2-nitro-3-[(3-tetrahydrofuryl)methyl]guanidine per 1m$^2$ of the fibrous product. Such an application amount of 1-methyl-2-nitro-3-[(3-tetrahydrofuryl)methyl]guanidine efficiently prevents the pest feed harm to the fibrous product for an extended amount of time.

Examples of application forms of 1-methyl-2-nitro-3-[(3-tetrahydrofuryl)methyl]guanidine include a spraying application, a spreading application, an eye-dropping application, a soaking application and the like. In the soaking application, 1-methyl-2-nitro-3-[(3-tetrahydrofuryl) methyl]guanidine may be added to a solution and the resulting solution may be utilized to soak the fibrous product.

The spraying application can be conducted by spraying the aerosol to the fibrous product, according with the conventional techniques. For example, the liquid compositions or the dilutions of the compositions may be pressure spray applied to the fibrous product. Examples of the liquid compositions which may be pressure spray applied include the oily composition, the emmulifiable concentrate, the suspension and the like. Examples of the compositions which may be diluted for the pressure spray application include the wettable powder, the microencapsulated composition and the like. To prepare the liquid composition or the dilution for the pressure spray application, the liquid composition or the dilution can be inserted into an aerosol container and the air therein can then be pressurized by electricity or by hand. The prepared liquid composition or the prepared dilution can then be sprayed onto the fibrous material. If needed, the resulting fibrous product may be allowed to dry thereafter.

The spreading application can be conducted by applying 1-methyl-2-nitro-3-[(3-tetrahydrofuryl)methyl]guanidine onto a brush or roller and then employing the brush or roller to spread 1-methyl-2-nitro-3-[(3-tetrahydrofuryl)methyl] guanidine onto the surface of the fibrous product. In such cases, the liquid composition, such as the foamy composition, the wettable powder or the dilutions thereof may be utilized to spread 1-methyl-2-nitro-3-[(3-tetrahydrofuryl)methyl]guanidine. If needed, the resulting fibrous product may be allowed to dry thereafter.

The eye-dropping application can be conducted by utilizing an eye-dropping device to allow 1-methyl-2-nitro-3-[(3-tetrahydrofuryl)methyl]guanidine to drip onto the fibrous product. In such cases, a pipette may be utilized as the eye-dropping device to drip dropwise onto the fibrous product, the liquid composition or the dilution. For example, the pipette may drip the dilution of the wettable powder onto the fibrous product. If needed, the resulting fibrous product may be allowed to dry thereafter.

The soaking application can be conducted by soaking the fibrous product with 1-methyl-2-nitro-3-[(3-tetrahydrofuryl) methyl]guanidine. In such cases, there may be utilized the liquid composition, the dilution of the liquid composition, the dilution of the wettable powder, the dilution of the microencapsulated composition and the like. If needed, the resulting fibrous product may be allowed to dry thereafter.

As pests which feed harm fibrous material, for example, there is mentioned household pests such as *Tinea translucens,* webbing clothes moth (*Tineola bisselliella*), *Attagenus unicolor,* varied carpet beetle (*Anthrenus verbasci*), hide beetles (*Dermestes maculates*), *Gibbium aequinoctiale* and the like.

The compositions of 1-methyl-2-nitro-3-[(3-tetrahydrofuryl)methyl]guanidine may have added thereto an additional active compound to prevent the pest feed harm on a fibrous product. Examples of such an additional active compound include pyrethroid compounds such as permethrin, phenothrin, allethrin, pyrethrin, prallethrin, cyphenothrin, cyfluthrin, fenvalerate, fenpropathrin, transfluthrin, bifenthrin, empenthrin, etofenprox and silafluofen; organophosphorous compounds such as fenitrothion, malathion, dichlorvos, tetrachlorvinphos, fenthion, chlorpyrifos and diazinon; carbamate compounds such as propoxur, carbaryl, metoxadiazone and fenobucarb; chitin synthesis inhibitors such as lufenuron, chlorfluazuron, hexaflumuron and cyromazine; juvenile hormone analogues such as methoprene, hydroprene and fenoxycarb; N-phenylpyrazole compounds; pest repellents such as N,N-diethyl-m-toluamide, limonene, linalool, citronellol, menthol, menthone, hinokitiol, geraniol, eucalyptol, indoxacarb, carane-3,4-diol, Paraben (parahydroxy benzoate), PCMX (4-chloro-3,5-dimethylphenol), thymol (6-isopropyl-m-cresol) and hinkithiol and the like.

Further, the compositions may also have added thereto synergists such as PBO, S421, MGK264, IBTA and the like.

EXAMPLES

The present invention is explained in further detail hereinafter with the examples.

Formulation Example 1

One-tenth (0.1) gram of 1-methyl-2-nitro-3-[(3-tetrahydrofuryl)methyl]guanidine is dissolved in 2 g of benzyl alcohol and is inserted into a aerosol container. Isopar-G (Exxon Chemicals) is then added thereto so that the resulting composition amounts to 20 g. After attaching an aerosol valve to the aerosol container, 80 g of dimethyl ether is packed into the aerosol container to produce 100 g of the aerosol of the present invention.

Formulation Example 2

Five-hundredths (0.05) grams of 1-methyl-2-nitro-3-[(3-tetrahydrofuryl)methyl]guanidine and 0.05 g of (E)-1-ethynyl-2-methyl-pent-2-enyl (1R)-cis,trans-chrysanthemate are dissolved in 3 g of ethyl alcohol and the resulting mixture is then inserted into an aerosol container. Isopar-G (Exxon Chemicals) is then added to the mixture so that the resulting composition amounts to 20 g. After attaching an aerosol valve to the aerosol container, 80 g of dimethyl ether is packed into the aerosol container to produce 100 g of the aerosol of the present invention.

Formulation Example 3

A composition is produced by mixing together 0.1 g of 1-methyl-2-nitro-3-[(3-tetrahydrofuryl)methyl]guanidine and 1 g of sodium citrate. Deionized water is then added to the composition to produce 100 g of the dilution of the present invention.

Formulation Example 4

A composition is produced by mixing together 0.1 g of 1-methyl-2-nitro-3-[(3-tetrahydrofuryl)methyl]guanidine, 1 g of citric acid, 0.1 g of dibutylhydroxytoluene (BHT) and 50 g of ethanol. Deionized water is then added to the composition to produce 100 g of the dilution of the present invention.

Test Example 1

One-tenth (0.1) milliliter of acetone solutions composed of 0.1% w/v and 0.3% w/v of 1-methyl-2-nitro-3-[(3-tetrahydrofuryl)methyl]guanidine (hereinafter referred to as the present compound), respectively, was eye-dropped with a pipette onto wool muslins. The application amounts thereof had 25 mg and 75 mg of the present compound uniformly applied per 1m$^2$ of the wool muslins. Each of the wool muslins had a height of 2 cm and a width of 2 cm.

Each of the resulting wool muslins was then allowed to dry and was placed on the bottom portion of a plastic container. The plastic container had a volume of 950 cm$^3$ and had the top portion thereof opened.

Ten (10) middle instar larvae webbing clothes moth (*Tineola bisselliella*) were then placed, respectively, into the plastic container, and a nylon net was set on the top portion of the plastic container to cover the opening thereof. After 7 days of infestation under 25±2° C., the pest feed harm on the wool muslins were examined. The standards to the pest feed harm were "+++" for a heavy level of the pest feed harm, "++" for a normal level of the pest feed harm, "+" for a minor level of the pest feed harm and "−" for no visual pest feed harm. The tests were repeated 5 times.

Further, as a control, a test utilizing a wool muslin to which no composition was applied was similarly conducted. The control was repeated twice. The results are shown in Table 1 below.

Comparative Example 1

One-tenth (0.1) milliliter of acetone solutions composed of 0.1% w/v and 0.3% w/v of (E)-1-ethynyl-2-methyl-pent-2-enyl-(1R)-cis,trans-chrysanthemate (hereinafter referred to as comparative compound 1), respectively, was eye-dropped with a pipette onto wool muslins. The application amounts thereof had 25 mg and 75 mg of comparative compound 1 uniformly applied per 1m$^2$ of the wool muslins. Each of the wool muslins had a height of 2 cm and a width of 2 cm.

Each of the resulting wool muslins was then allowed to dry and was placed on the bottom portion of a plastic container. The plastic container had a volume of 950 cm$^3$ and had the top portion thereof opened.

Ten (10) middle instar larvae webbing clothes moth (*Tineola bisselliella*) were then placed, respectively, into the plastic container, and a nylon net was set on the top portion of the plastic container to cover the opening thereof. After 7 days of infestation under 25±2° C., the pest feed harm on the wool muslins were examined. The standards to the pest feed harm were "+++" for a heavy level of the pest feed harm, "++" for a normal level of the pest feed harm, "+" for a minor level of the pest feed harm and "−" for no visual pest feed harm. The comparative experiments were repeated 5 times. The results are shown in Table 1 below.

TABLE 1

| No. | Active compound | Application amount (mg/m$^2$) | Pest feed harm 1 | 2 | 3 | 4 | 5 |
|---|---|---|---|---|---|---|---|
| Test Example 1 | Present compound | 25 | − | − | − | − | − |
| Test Example 1 | Present compound | 75 | − | − | − | − | − |
| Comparative Example 1 | Comparative compound 1 | 25 | + + | + + | + | + + | + |
| Comparative Example 1 | Comparative compound 1 | 75 | + | + | + | + + | + |
| Control | None | | + + + | + + + | | | |

Test Example 2

One-tenth (0.1) milliliter of acetone solutions composed of 0.1% w/v and 0.3% w/v of the present compound, respectively, was eye-dropped with a pipette onto wool muslins. The application amounts thereof had 25 mg and 75 mg of the present compound uniformly applied per 1m$^2$ of the wool muslins. Each of the wool muslins had a height of 2 cm and a width of 2 cm.

Each of the resulting wool muslins was then preserved at 25±2° C. for 2 weeks. After the 2 weeks, each of the wool muslins was placed on the bottom portion of a plastic container. The plastic container had a volume of 950 cm$^3$ and had the top portion thereof opened.

Ten (10) middle instar larvae webbing clothes moth (*Tineola bisselliella*) were then placed, respectively, into the plastic container and a nylon net was set on the top portion of the plastic container to cover the opening thereof. After 7 days of infestation under 25±2° C., the pest feed harm on the wool muslins were examined. The standards to the pest feed harm were "+++" for a heavy level of the pest feed harm, "++" for a normal level of the pest feed harm, "+" for a minor level of the pest feed harm and "−" for no visual feed harm. The tests were repeated 5 times.

Further, as a control, a test utilizing a wool muslin to which no composition was applied was similarly conducted.

The control was repeated twice. The results are shown in Table 2 below.

Comparative Example 2

One-tenth (0.1) milliliter of acetone solutions composed of 0.1% w/v and 0.3% w/v of Comparative compound 1, respectively, was eye-dropped with a pipette onto wool muslins. The application amounts thereof had 25 mg and 75 mg of Comparative compound 1 uniformly applied per $1m^2$ of the wool muslins. Each of the wool muslins had a height of 2 cm and a width of 2 cm.

Each of the resulting wool muslins was then preserved at 25±2° C. for 2 weeks. After the 2 weeks, each of the wool muslins was placed on the bottom portion of a plastic container. The plastic container had a volume of 950 $cm^3$ and had the top portion thereof opened.

Ten (10) middle instar larvae webbing clothes moth (*Tineola bisselliella*) were then placed, respectively, into the plastic container and a nylon net was set on the top portion of the plastic container to cover the opening thereof. After 7 days of infestation under 25±2° C., the pest feed harm on the wool muslins were examined. The standards to the pest feed harm were "+++" for a heavy level of the pest feed harm, "++" for a normal level of the pest feed harm, "+" for a minor level of the pest feed harm and "−" for no visual pest feed harm. The comparative experiments were repeated 5 times. The results are shown in Table 2 below.

TABLE 2

| No. | Active compound | Application amount (mg/m²) | Pest feed harm | | | | |
|---|---|---|---|---|---|---|---|
| | | | 1 | 2 | 3 | 4 | 5 |
| Test Example 2 | Present compound | 25 | − | − | − | − | − |
| Test Example 2 | Present compound | 75 | − | − | − | − | − |
| Comparative Example 1 | Comparative compound 1 | 25 | +++ | +++ | +++ | +++ | +++ |
| Comparative Example 1 | Comparative compound 1 | 75 | +++ | +++ | +++ | +++ | +++ |
| Control | None | | +++ | +++ | | | |

What is claimed is:

1. A method of preventing pest feed harm on a fibrous product, said method comprising:

applying to a fibrous product, an effective amount of 1-methyl-2-nitro-3-(3-tetrahxrdrofuryl)methyl] guanidine wherein the fibers of the fibrous product are selected from the group consisting of wool, cotton, fur, hemp, silk, and mixtures thereof to prevent said pest feed harm.

2. The method according to claim 1, wherein the effective amount is 1 mg/1 $m^2$ to 5000 mg/$m^2$ of 1-methyl-2-nitro-3-[(3-tetrahydrofuryl)methyl-guanidine, wherein said square meters are based on the area of the fibrous product.

3. The method according to claim 1, wherein the fibrous product is at least one fibrous product selected from the group consisting of a floor rug, a carpet and a cloth.

4. The method according to claim 1, wherein the fibrous product is at least one fibrous product selected from clothing, textile, floor rug, carpet, floor mat, and fibrous furniture cushion.

* * * * *